United States Patent
Kim et al.

(10) Patent No.: US 10,322,982 B2
(45) Date of Patent: Jun. 18, 2019

(54) ENERGY SAVING METHOD AND APPARATUS FOR PREPARING STYRENE AND ALPHA-METHYLSTYRENE CONCURRENTLY

(71) Applicant: LG CHEM, LTD., Seoul (KR)

(72) Inventors: Mi-Kyung Kim, Daejeon (KR); Jae-Ik Lee, Daejeon (KR); Jong-Ku Lee, Daejeon (KR); Jeong-Seok Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/760,899

(22) PCT Filed: Dec. 7, 2016

(86) PCT No.: PCT/KR2016/014331
§ 371 (c)(1),
(2) Date: Mar. 16, 2018

(87) PCT Pub. No.: WO2017/111356
PCT Pub. Date: Jun. 29, 2017

(65) Prior Publication Data
US 2018/0273445 A1    Sep. 27, 2018

(30) Foreign Application Priority Data

Dec. 22, 2015  (KR) .................. 10-2015-0184200
Nov. 11, 2016  (KR) .................. 10-2016-0150577

(51) Int. Cl.
*C07C 5/327* (2006.01)
*C07C 5/32* (2006.01)
(Continued)

(52) U.S. Cl.
CPC .............. *C07C 5/327* (2013.01); *B01J 19/24* (2013.01); *B01J 21/04* (2013.01); *B01J 21/08* (2013.01);
(Continued)

(58) Field of Classification Search
CPC ........ C07C 5/32; C07C 5/327; B01J 2219/00; B01J 2219/00027
(Continued)

(56) References Cited

U.S. PATENT DOCUMENTS 3,256,355 A * 6/1966 Gilman .................... C07C 7/04
203/21
4,628,136 A   12/1986 Sardina
(Continued)

FOREIGN PATENT DOCUMENTS

KR        89-0001849 B1    5/1989
KR   10-2015-0088892 A    8/2015
(Continued)

OTHER PUBLICATIONS

Search Report issued by the European Patent Office in Appl'n No. 16879223.2, dated Nov. 13, 2018.

*Primary Examiner* — Thuan D Dang
(74) *Attorney, Agent, or Firm* — Dentons US LLP

(57) ABSTRACT

The present invention relates to energy saving method and apparatus for preparing styrene and alpha-methylstyrene concurrently, by which economic feasibility may be improved by reusing energy during preparing styrene and alpha-methylstyrene concurrently.

20 Claims, 4 Drawing Sheets

(51) Int. Cl.
- *B01J 21/04* (2006.01)
- *B01J 21/08* (2006.01)
- *B01J 23/28* (2006.01)
- *B01J 23/30* (2006.01)
- *B01J 23/31* (2006.01)
- *B01J 23/40* (2006.01)
- *B01J 23/745* (2006.01)
- *C07C 7/04* (2006.01)
- *B01J 19/24* (2006.01)
- *C07C 5/333* (2006.01)
- *C07C 7/00* (2006.01)
- *C07C 7/09* (2006.01)

(52) U.S. Cl.
CPC ............ *B01J 23/28* (2013.01); *B01J 23/30* (2013.01); *B01J 23/31* (2013.01); *B01J 23/40* (2013.01); *B01J 23/745* (2013.01); *C07C 5/333* (2013.01); *C07C 7/005* (2013.01); *C07C 7/04* (2013.01); *C07C 7/09* (2013.01); *B01J 2219/00103* (2013.01); *B01J 2219/24* (2013.01); *C07C 2521/04* (2013.01); *C07C 2521/08* (2013.01); *C07C 2523/02* (2013.01); *C07C 2523/06* (2013.01); *C07C 2523/10* (2013.01); *C07C 2523/16* (2013.01); *C07C 2523/40* (2013.01); *C07C 2523/70* (2013.01); *Y02P 20/124* (2015.11); *Y02P 20/51* (2015.11)

(58) Field of Classification Search
USPC .......................... 585/440, 441; 422/198, 608
See application file for complete search history.

(56) References Cited

U.S. PATENT DOCUMENTS

| | | |
|---|---|---|
| 2006/0135831 A1 | 6/2006 | Butler et al. |
| 2007/0225532 A1 | 9/2007 | Tonkovich et al. |
| 2009/0043142 A1 | 2/2009 | Lucchini et al. |
| 2009/0312590 A1 | 12/2009 | Schwint et al. |
| 2011/0112348 A1 | 5/2011 | Tonkovich et al. |
| 2015/0336859 A1 | 11/2015 | Welch |
| 2017/0007978 A1 | 1/2017 | Tonkovich et al. |

FOREIGN PATENT DOCUMENTS

| | | |
|---|---|---|
| WO | 2004-060839 A1 | 7/2004 |
| WO | 2007/073918 A1 | 7/2007 |
| WO | 2014/098816 A1 | 6/2014 |

\* cited by examiner

ENERGY SAVING METHOD AND APPARATUS FOR PREPARING STYRENE AND ALPHA-METHYLSTYRENE CONCURRENTLY

TECHNICAL FIELD

This application is a National Stage Entry of International Application No. PCT/KR2016/014331 filed on Dec. 7, 2016, and claims the benefit of Korean Application No. 10-2015-0184200, filed on Dec. 22, 2015, and Korean Application No. 10-2016-0150577, filed on Nov. 11, 2016, all of which are hereby incorporated by reference in their entirety for all purposes as if fully set forth herein.

The present invention relates to energy saving method and apparatus for preparing styrene and alpha-methylstyrene concurrently, and more particularly, to energy saving method and apparatus for preparing styrene and alpha-methylstyrene concurrently, by which economic feasibility may be improved by reusing energy during preparing styrene and alpha-methylstyrene concurrently.

BACKGROUND ART

Alpha-methylstyrene (AMS) is mainly used as a comonomer for high heat resistance and for improving impact physical properties of acrylonitrile butadiene styrene (ABS), polystyrene (PS) and acrylic resins, and in addition, is used as a coating agent, adhesives, cumylphenol, wax, or the like. Such alpha-methylstyrene (AMS) is mostly produced commercially as the by-products of a cumene (CM) oxidation reaction in a bisphenol-A (BPA) process, and also, as shown in Reaction 1 below, may be obtained by the dehydrogenation reaction of cumene, which is not used commercially.

[Reaction 1]

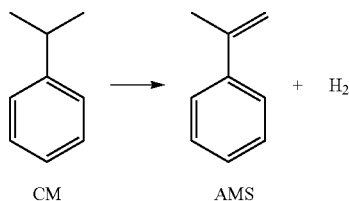

CM       AMS

However, the method is very similar to the production technique of styrene (SM; styrene monomer) in which ethylbenzene (EB) is dehydrogenated in view of technical aspect, as shown in Reaction 2 below, and by-products mainly include materials produced during preparing styrene (SM), such as toluene, ethylbenzene and styrene. Thus, alpha-methylstyrene may be obtained with low investment costs by modifying the conventional preparation process of styrene and feeding ethylbenzene and cumene concurrently to produce styrene and alpha-methylstyrene (AMS) concurrently when compared to a case of producing solely.

[Reaction 2]

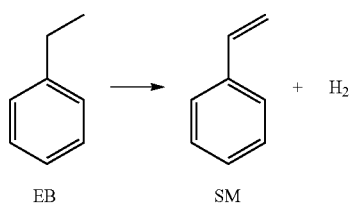

EB       SM

Meanwhile, FIG. 1 is a diagram partially showing a common styrene preparation process. Styrene (SM) is prepared by reacting ethylbenzene (EB) and undergoing processes such as condensation and fractional distillation. Since the difference of boiling points between ethylbenzene and styrene is small, a lot of energy is required for the separation of EB/SM. In order to solve this, as shown in FIG. 1, instead of using a utility such as steam in a reboiler of EB/SM separation column, waste heat in a process is utilized, or heat of a condenser is recovered and utilized instead of steam. Generally, recovered heat from the condenser of EB/SM separation column is used for the vaporization of ethylbenzene which is injected to a reactor, and in this case, an azeotropic mixture of ethylbenzene/water is vaporized to decrease a vaporization temperature and increase heat recovery. Accordingly, a highly economic method for producing styrene and alpha-methylstyrene concurrently and for decreasing the amount of energy consumed for the production is required by modifying the conventional styrene process.

DISCLOSURE OF THE INVENTION

Technical Problem

As examined above, a lot of energy is required for the conventional preparation process of styrene, and in order to produce styrene and alpha-methylstyrene concurrently by modifying and transforming such conventional preparation process of styrene, the reduction of energy which is used in a process is acutely required.

Accordingly, an object of the present invention to solve the aspect is to provide energy saving method and apparatus for preparing styrene and alpha-methylstyrene concurrently, by which economic feasibility may be improved by reusing energy during preparing styrene and alpha-methylstyrene concurrently.

Technical Solution

In order to accomplish the object, the present invention provides an energy saving method for preparing styrene and alpha-methylstyrene concurrently, comprising: (a) a step of performing dehydrogenation reaction of ethylbenzene and cumene in the presence of a catalyst; (b) a step of recovering heat from a reaction product by the reaction; (c) a step of separating a gas phase from at least a portion of a reaction product undergone step (b) and sending thereof to a compression part, separating condensing water including water from a liquid phase, and recovering a fraction including styrene and alpha-methylstyrene; (d) a step of compressing and cooling at least a portion of a gas phase among reaction products undergone step (c) to separate components having a low boiling point including hydrogen and carbon dioxide as a gas phase, and recycle a liquid phase including styrene, alpha-methylstyrene, ethylbenzene and cumene to step (c); (e) a step of distilling and separating at least a portion of the fraction including styrene and alpha-methylstyrene, which is recovered in step (c), into a fraction including styrene and a fraction including unreacted cumene; (f) a step of recovering styrene from at least a portion of the fraction including styrene and distilling and separating the fraction including unreacted ethylbenzene of step (e); (g) a step of recovering ethylbenzene from at least a portion of the fraction including unreacted ethylbenzene of step (f) and recycling to a reaction part, and distilling and separating the fraction including benzene and toluene; (h) a step of recovering cumene from at least a portion of the fraction including unreacted cumene of step (e) and recycling the recovered cumene to a reaction part, and distilling and separating a fraction including alpha-methylstyrene; and (i) a step of recovering alpha-methylstyrene from at least a portion of the fraction including alpha-methylstyrene of step (h), and distilling and separating a fraction including a remaining component having a high boiling point, wherein at least one of energy used during the distilling and separating in step (e) and energy used during the distilling and separating in step (h) is recovered to use for the vaporization of ethylbenzene and cumene of step (a) or as a heat source of a preparation process.

In addition, the present invention provides an energy saving apparatus for preparing styrene and alpha-methylstyrene concurrently, comprising: a reactor for performing dehydrogenation reaction of ethylbenzene and cumene in the presence of catalyst; a heat exchanger for recovering heat from a reaction product from the reaction; a decanter for separating a gas phase from at least a portion of a reaction product from which heat is recovered and sending thereof to a compression part, for separating condensing water including water from a liquid phase, and for recovering a fraction including styrene and alpha-methylstyrene; a compression part composed of a compressor, a heat exchanger and a drum, for compressing and cooling at least a portion of the separated gas phase to separate components having a low boiling point including hydrogen and carbon dioxide as a gas phase, and for recovering a liquid phase including styrene, alpha-methylstyrene, ethylbenzene and cumene; an SM/CM separation column for distilling and separating at least a portion of the fraction including styrene and alpha-methylstyrene, supplied from the decanter into a fraction including styrene and a fraction including unreacted cumene; an EB/SM separation column for recovering styrene from at least a portion of the fraction including styrene separated from the SM/CM separation column, and distilling and separating a fraction including unreacted ethylbenzene; an EB purification column for recovering ethylbenzene from at least a portion of the fraction including unreacted ethylbenzene, separated from the EB/SM separation column and recycling the recovered ethylbenzene to the reactor, and distilling and separating a fraction including benzene and toluene; a CM/AMS separation column for recovering cumene from at least a portion of the fraction including unreacted cumene, separated from the SM/CM separation column, and recycling the recovered cumene to the reactor, and distilling and separating a fraction including alpha-methylstyrene; an AMS purification column for recovering alpha-methylstyrene from at least a portion of the fraction including alpha-methylstyrene, separated from the CM/AMS separation column, and distilling and separating a fraction including a remaining component having a high boiling point; an EB vaporizer for receiving energy used in the SM/CM separation column and the CM/AMS separation column, and for using the energy for the vaporization of ethylbenzene which undergoes dehydrogenation reaction in the reactor or for using as a heat source of a preparation process; and a CM vaporizer for receiving energy used in the SM/CM separation column and the CM/AMS separation column, and for using for the vaporization of cumene which undergoes dehydrogenation reaction in the reactor or for using as a heat source of a preparation process.

Advantageous Effects

According to the energy saving method and apparatus for preparing styrene and alpha-methylstyrene concurrently, economic feasibility may be improved by reusing energy for preparing styrene and alpha-methylstyrene concurrently. Besides, since styrene and alpha-methylstyrene may be prepared concurrently by modifying the conventional styrene preparation process, alpha-methylstyrene may be prepared with low investment costs.

BEST MODE FOR CARRYING OUT THE INVENTION

Hereinafter, the present invention will be described in more detail referring to attached drawings.

Figure 2:
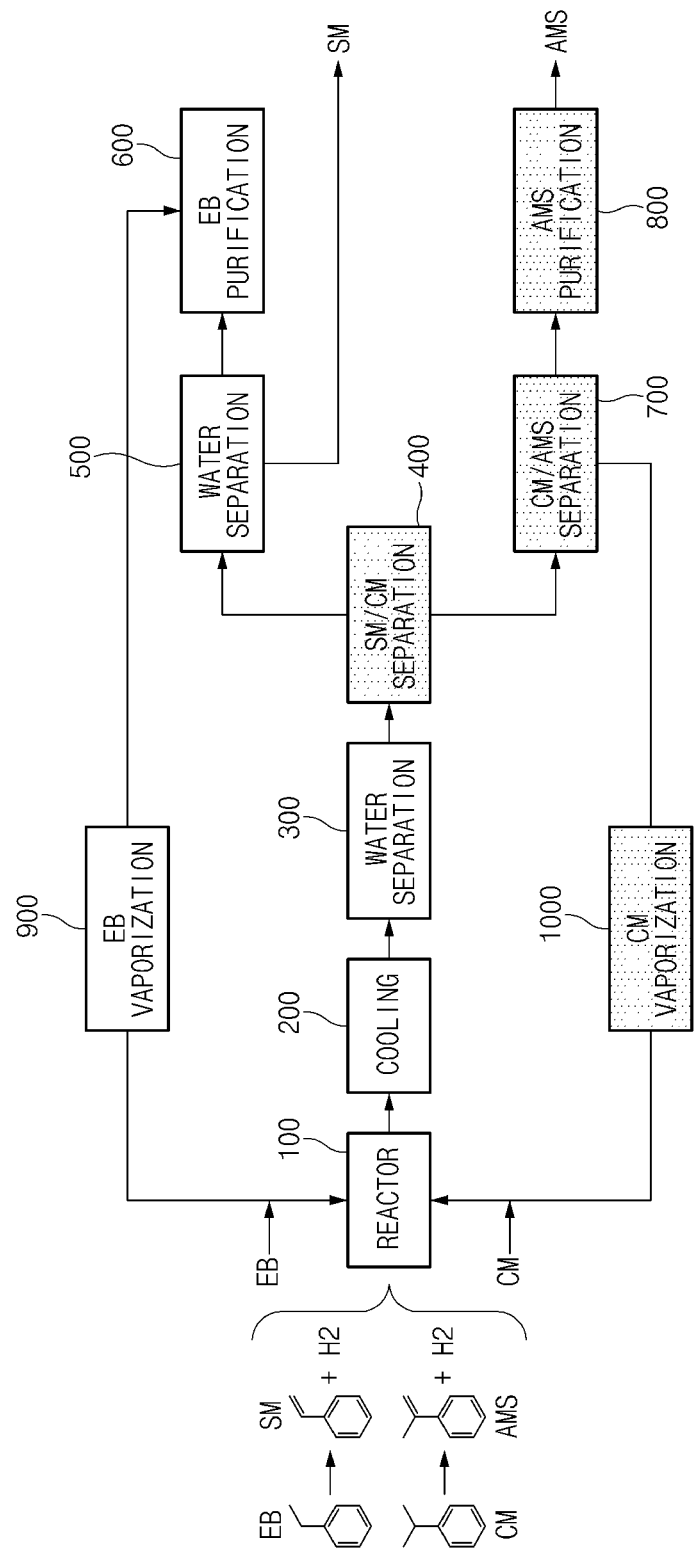
FIG. 2 is a schematic process diagram for explaining energy saving method and apparatus for preparing styrene and alpha-methylstyrene concurrently according to the present invention.

FIG. 2 is a schematic process diagram for explaining energy saving method and apparatus for preparing styrene and alpha-methylstyrene concurrently according to the present invention. The energy saving method for preparing styrene and alpha-methylstyrene concurrently according to the present invention comprises (a) a step of performing dehydrogenation reaction of ethylbenzene (EB) and cumene (CM) in the presence of a catalyst; (b) a step of recovering heat from a reaction product by the reaction; (c) a step of separating a gas phase from at least a portion of a reaction product undergone step (b) and sending thereof to a compression part, separating condensing water including water from a liquid phase, and recovering a fraction including styrene and alpha-methylstyrene; (d) a step of compressing and cooling at least a portion of a gas phase among reaction products undergone step (c) to separate components having a low boiling point including hydrogen and carbon dioxide as a gas phase, and recycle a liquid phase including styrene, alpha-methylstyrene, ethylbenzene and cumene to step (c); (e) a step of distilling and separating at least a portion of the fraction including styrene and alpha-methylstyrene, which is recovered in step (c), into a fraction including styrene and a fraction including unreacted cumene; (f) a step of recovering styrene from at least a portion of the fraction including styrene and distilling and separating the fraction including unreacted ethylbenzene of step (e); (g) a step of recovering ethylbenzene from at least a portion of the fraction including unreacted ethylbenzene of step (f) and recycling to a reaction part, and distilling and separating the fraction including benzene and toluene; (h) a step of recovering cumene from at least a portion of the fraction including unreacted cumene of step (e) and recycling the recovered cumene to a reaction part, and distilling and separating a fraction including alpha-methylstyrene; and (i) a step of recovering alpha-methylstyrene from at least a portion of the fraction including alpha-methylstyrene of step (h), and distilling and separating a fraction including a remaining component having a high boiling point, wherein at least one of energy used during the distilling and separating in step (e) and energy used during the distilling and separating in step (h) is recovered to use for the vaporization of ethylbenzene and cumene of step (a) or as a heat source of a preparation process.

In order to prepare styrene and alpha-methylstyrene concurrently according to the present invention, first, (a) dehydrogenation reaction of ethylbenzene and cumene used as feeds is performed in the presence of catalyst. That is, in step (a), as shown in FIG. 2, the ethylbenzene and cumene form styrene and alpha-methylstyrene concurrently and respectively by dehydrogenation reaction by using a method of supplying ethylbenzene and cumene to one reactor (100) which was not present before.

The catalyst added to the dehydrogenation reaction of ethylbenzene and cumene may include any one for used for dehydrogenating ethylbenzene and cumene to produce styrene and alpha-methylstyrene, without limitation. Examples include iron oxides, palladium, platinum, aluminum oxides, silicon oxides, ruthenium, rhenium, osmium, rhodium, iridium, cerium, molybdenum, tungsten, vanadium, bismuth, magnesium, potassium, calcium, copper, zinc, arsenic, antimony, ferrochromium, cobalt, and a mixture thereof. Meanwhile, the ratio of ethylbenzene and cumene supplied to the reactor (100) (or used in dehydrogenation reaction) is about 0.1-10:1 by weight, and may be flexibly changed according to market prices.

The dehydrogenation reaction is performed at a temperature of 300 to 800° C., preferably, 550 to 650° C. In addition, steam which may be supplied during the dehydrogenation reaction is for improving the stability and selectivity of reaction, and the amount used is steam:reactant (ethylbenzene and cumene)=3-20:1, preferably, 6-12:1 in a mole ratio.

Then, when the product by the dehydrogenation reaction of step (a) is discharged from the reactor (100), (b) a process for recovering heat from the reaction product by the reaction is performed, and in this case, the reaction product is cooled in a heat exchanger (200) to about 15 to 60° C., preferably, about 50 to 60° C. Meanwhile, heat recovered from the reaction product may be used as energy required in an internal process or in an external process.

After recovering heat from the reaction product of step (b), (c) a gas phase is separated from at least a portion of the reaction product from which heat is recovered and is sent to a compression part (not shown), condensing water including water is separated from a liquid phase, and a fraction including styrene (SM) and alpha-methylstyrene (AMS) is recovered. The process of step (c) is performed in a decanter (300), and the condensing water separated may be reused in a process or discarded.

In succession, (d) at least a portion of a gas phase among reaction products undergone step (c) is compressed and cooled to separate components having a low boiling point including hydrogen and carbon dioxide as a gas phase (or gaseous phase) (that is, separating light gas), a liquid phase including styrene, alpha-methylstyrene, ethylbenzene and cumene is recycled to step (c), in other words, to the decanter (300). The recycling of the liquid phase including styrene, alpha-methylstyrene, ethylbenzene and cumene to step (c), means the recovering of effective components including styrene, alpha-methylstyrene, ethylbenzene and cumene in a liquid phase and recycling to the decanter (300). In this case, in the compression part (not shown), the reaction product is compressed until a pressure becomes to about 1.5 to 5.5 KCA (kgf/cm$^2$a), preferably, about 1.5 to 2.5 KCA. Meanwhile, the compression part is composed of a compressor, a heat exchanger and a drum.

Then, (e) at least a portion of the fraction including styrene and alpha-methylstyrene, which is recovered in step (c) (in other words, supplied from the decanter (300)) is distilled and separated into a fraction including styrene and a fraction including unreacted cumene. The process of step (e) is performed in an SM/CM separation column (400), where (unreacted) cumene (CM, boiling point: 152.41° C.) which has a relatively higher boiling point than styrene (SM, boiling point: 145.16° C.) is discharged via the bottom part of the SM/CM separation column (400), and styrene is discharged via the top part of the SM/CM separation column (400). In addition, the pressure of the SM/CM separation column (400) is from 0.01 to 5 KCA, preferably, from 0.1 to 1 KCA.

Then, (f) styrene is recovered from at least a portion of the fraction including styrene of step (e), and the fraction including unreacted ethylbenzene is distilled and separated. The process of step (f) is performed in an EB/SM separation column (500), where styrene (SM, boiling point: 145.16° C.) which has a relatively higher boiling point than ethylbenzene (EB, boiling point: 136.2° C.) is discharged via the bottom part of the EB/SM separation column (500) and recovered, and a fraction including unreacted ethylbenzene is discharged via the top part of the BM/SM separation column (500). In addition, the pressure of the EB/SM separation column (500) is from 0.01 to 6 KCA, preferably, from 0.1 to 1 KCA.

Then, (g) ethylbenzene is recovered from at least a portion of the fraction including unreacted ethylbenzene of step (f) and sent to a reaction part, and a fraction including benzene and toluene is distilled and separated. The process of step (g) is performed in an EB purification column (600), where ethylbenzene (EB, boiling point: 136.2° C.) which has a relatively higher boiling point than toluene (boiling point: 110.63° C.) is discharged via the bottom part of the EB purification column (600), recovered and sent to a reaction part (or the reactor (100)) where the dehydrogenation reaction is performed, and a fraction including benzene and toluene is discharged via the top part of the EB purification column (600). The benzene and toluene are by-products produced during the dehydrogenation reaction and the separation process, but may be usefully used if recovered using an additional installment. In addition, the pressure of the EB purification column (600) is from 0.01 to 7 KCA, preferably, from 1 to 2 KCA.

In succession, (h) cumene is recovered from at least a portion of the fraction including unreacted cumene of step (e) and recycled to a reaction part, and a fraction including alpha-methylstyrene is distilled and separated. The process of step (h) is performed in a CM/AMS separation column (700), where cumene (boiling point: 152.41° C.) which has a relatively lower boiling point than alpha-methylstyrene (AMS, boiling point: 165.5° C.) is discharged via the top part of the CM/AMS separation column (700), recovered and recycled to a reaction part (or the reactor (100)), and a fraction including alpha-methylstyrene is discharged via the bottom part of the CM/AMS separation column (700). In addition, the pressure of the CM/AMS separation column (700) is from 0.01 to 8 KCA, preferably, from 0.1 to 1 KCA.

Finally, (i) alpha-methylstyrene is recovered from at least a portion of the fraction including alpha-methylstyrene of step (h), and a fraction including a remaining component having a high boiling point is distilled and separated. The process of step (i) is performed in an AMS purification column (800), where alpha-methylstyrene (AMS, boiling point: 165.5° C.) which has a relatively lower boiling point than remaining component having a high boiling point (boiling point: greater than 165.5° C.) is discharged via the top part of the AMS purification column (800) and recovered, and the remaining component having a high boiling point is discharged via the bottom part of the AMS purification column (800). In addition, the pressure of the AMS purification column (800) is from 0.01 to 9 KCA, preferably, from 0.5 to 1.5 KCA.

Meanwhile, the styrene recovery of step (f) which is performed after step (e) and the alpha-methylstyrene recovery of step (i) are performed concurrently, but the order of the performance is not specifically limited, and one of the styrene recovery of step (f) or the alpha-methylstyrene recovery of step (i) may be performed first, if convenient.

Figure 1:
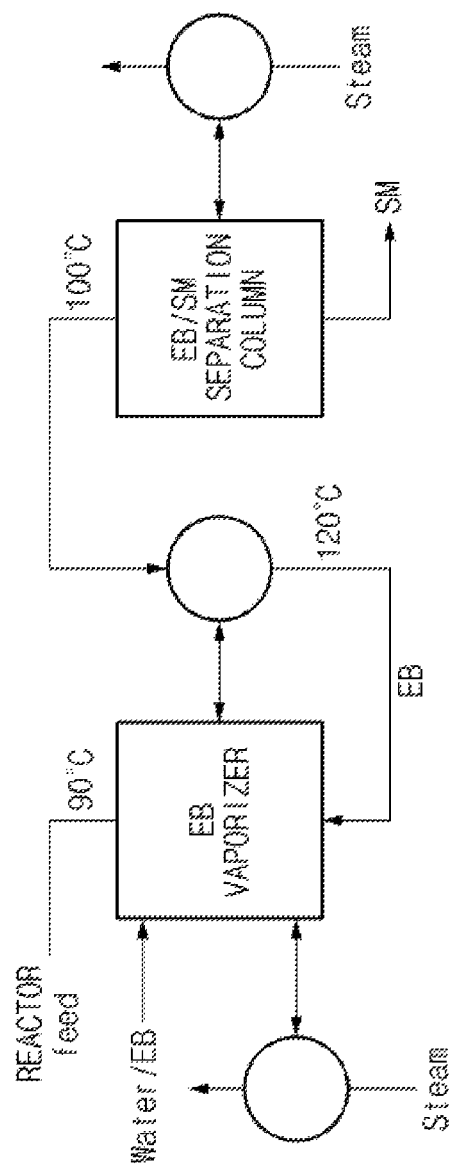
FIG. 1 is a diagram partially showing a common styrene preparation process.
Figure 3A:
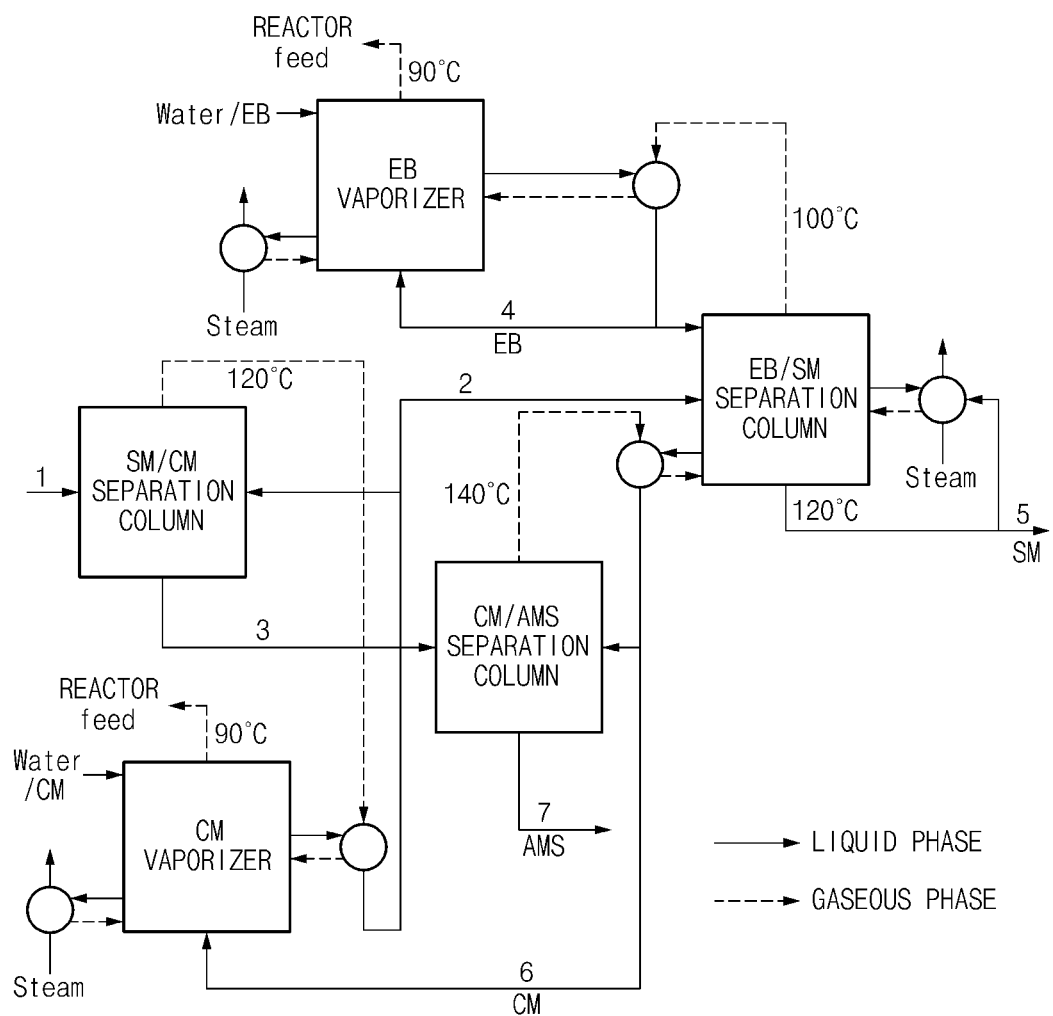
FIG. 3A and FIG. 3B illustrate partial process diagrams for showing an SM/CM separation column for separating styrene and cumene in energy saving method and apparatus for preparing styrene and alpha-methylstyrene concurrently according to the present invention.
Figure 3B:
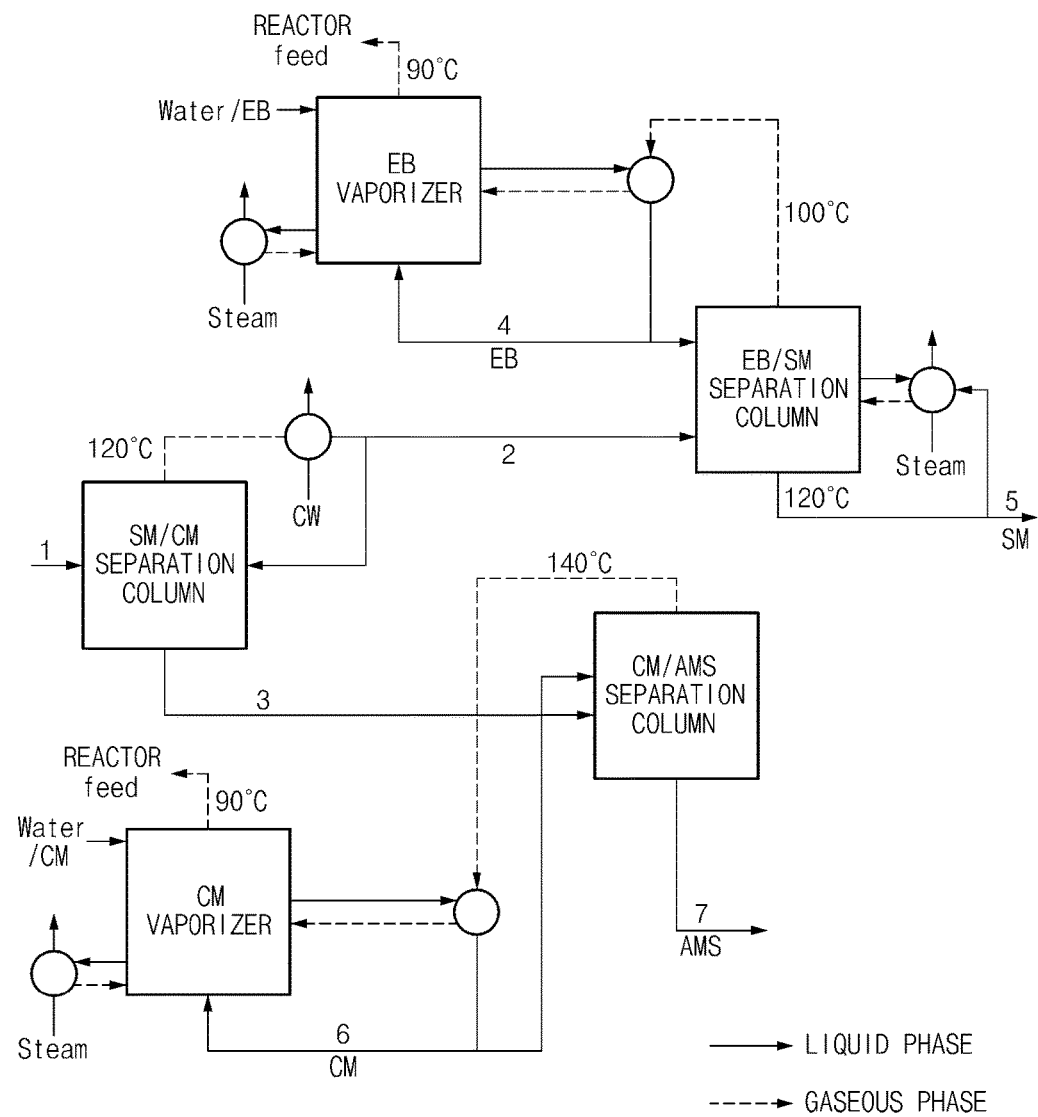

FIG. 3A and FIG. 3B illustrate partial process diagrams for showing an SM/CM separation column for separating styrene and cumene in energy saving method and apparatus for preparing styrene and alpha-methylstyrene concurrently according to the present invention, where FIG. 3A is a partial process diagram according to an embodiment of the present invention, and FIG. 3B is a partial process diagram according to another embodiment of the present invention. As shown in FIG. 3A and FIG. 3B, it is found that the energy saving process for preparing styrene and alpha-methylstyrene concurrently according to the present invention additionally includes an SM/CM separation column, a CM/AMS separation column, an AMS purification column and a CM vaporizer when compared to a common preparation method of styrene shown in FIG. 1. Among the additional process apparatuses, the SM/CM separation column has a large amount of energy used, because the difference of the boiling points between SM and CM, which are targets to be separated, is small. Thus, if the energy is recovered and reused, the energy amount used in total processes may be decreased, and economic feasibility may be improved.

That is, as described above, the characteristic of the present invention is the preparation of styrene and alpha-methylstyrene concurrently in a process, but the basic characteristic of the present invention intended to put more emphasis is the improvement of economic feasibility of a process by recovering energy used during distilling in the SM/CM separation column (400) of step (e) (in other words, heat used in a condenser of the SM/CM separation column (400)) (see FIG. 3A), or recovering energy used during distilling in the CM/AMS separation column (700) of step (h) (in other words, heat used in a condenser of the CM/AMS separation column (700) (see FIG. 3B), and using the recovered energy for the vaporization of ethylbenzene and cumene, which undergo dehydrogenation reaction in step (a) or as a heat source in a preparation process.

First, as shown in FIG. 3A, when examining a case of recovering energy used during distilling in the SM/CM separation column (400) of step (e), the energy used during distilling in the SM/CM separation column (400) is the greatest in this process, and this energy is required to be recovered as much as possible. It is important to increase heat exchange as much as possible in consideration of the operation temperature of a separation column and a vaporizer (EB vaporizer (900 of FIG. 2) and CM vaporizer (1000 of FIG. 2)). Styrene has the property of forming a polymer at a high temperature, and the operation temperature at the top part of the SM/CM separation column (400) is limited to about 120° C. or less. Accordingly, energy recovered from the SM/CM separation column (400) (accurately, heat of a condenser of the SM/CM separation column (400)) is preferably applied (used) in an EB vaporizer (900) or a CM vaporizer (1000), which are operated at about 100° C. or less. Energy supplied to the EB vaporizer (900) or the CM vaporizer (1000) vaporizes the feed of a reactor, accurately, ethylbenzene and cumene, respectively. In this case, to increase the recovering amount of heat by decreasing the vaporization temperature, an azeotropic mixture of ethylbenzene/water may be heated, and scant quantity of heat may be supplied using steam. Meanwhile, the heat of the condenser of the CM/AMS separation column (700) of which operation temperature is high and about 140° C., may be applied as the heat source of the reboiler of the EB/SM separation column (500).

Then, as shown in FIG. 3B, when examining a case of recovering energy used during distilling in the CM/AMS separation column (700) of step (h), since a difference of boiling points between CM and AMS, which are targets for separation of the CM/AMS separation column (700), is large, heat used in the CM/AMS separation column (700) is also small. This means that energy supplied to a CM vaporizer (1000) from the CM/AMS separation column (700) is also small, and in this case, the amount of steam supplied to the CM vaporizer (1000) is relatively increased. Meanwhile, in this case, energy supplied to the CM vaporizer from the CM/AMS separation column (700) is also applied for the vaporization of the feed of a reactor, accurately, cumene. In addition, the distillation of the CM/AMS separation column (700) of step (h) is performed at 140° C. or less, and energy used in the CM/AMS separation column (700) may be used for the distilling of the EB/SM separation column (500) of step (f) which is performed at 120° C. or less. Besides, the vaporization of ethylbenzene and cumene may be performed by energy used for distilling in the SM/CM separation column (400) of step (e) and in the CM/AMS separation column (700) of step (h), in addition, by further supplied steam of a separately installed steam apparatus.

In succession, referring to FIGS. 2 and 3, the energy saving apparatus for preparing styrene and alpha-methylstyrene concurrently according to the present invention will be explained. The energy saving apparatus for preparing styrene and alpha-methylstyrene concurrently according to the present invention comprises, as shown in FIG. 2, a reactor (100) for performing dehydrogenation reaction of ethylbenzene and cumene in the presence of catalyst; a heat exchanger (200) for recovering heat from a reaction product from the reaction; a decanter (300) for separating a gas phase from at least a portion of a reaction product from which heat is recovered and sending thereof to a compression part, for separating condensing water including water from a liquid phase, and for recovering a fraction including styrene and alpha-methylstyrene; a compression part (not shown) composed of a compressor, a heat exchanger and a drum, for compressing and cooling at least a portion of the separated gas phase to separate components having a low boiling point including hydrogen and carbon dioxide as a gas phase, and for recovering a liquid phase including styrene, alpha-methylstyrene, ethylbenzene and cumene; an SM/CM separation column (400) for distilling and separating at least a portion of the fraction including styrene and alpha-methylstyrene, supplied from the decanter (300) into a fraction including styrene and a fraction including unreacted cumene; an EB/SM separation column (500) for recovering styrene from at least a portion of the fraction including styrene separated from the SM/CM separation column (400), and distilling and separating a fraction including unreacted ethylbenzene; an EB purification column (600) for recovering ethylbenzene from at least a portion of the fraction including unreacted ethylbenzene, separated from the EB/SM separation column (500) and recycling the recovered ethylbenzene to the reactor (100), and distilling and separating a fraction including benzene and toluene; a CM/AMS separation column (700) for recovering cumene from at least a portion of the fraction including unreacted cumene, separated from the SM/CM separation column (400), and recycling the recovered cumene to the reactor (100), and distilling and separating a fraction including alpha-methylstyrene; an AMS purification column (800) for recovering alpha-methylstyrene from at least a portion of the fraction including alpha-methylstyrene, separated from the CM/AMS separation column (700), and distilling and separating a fraction including a remaining component having a high boiling point; an EB vaporizer (900) for receiving energy used in the SM/CM separation column (400) and the CM/AMS separation column (700), and for using the energy for the vaporization of ethylbenzene which undergoes dehydrogenation reaction in the reactor ( ) 100 or for using as a heat source of a preparation process; and a CM vaporizer (1000) for receiving energy used in the SM/CM separation column (400) and the CM/AMS separation column (700), and for using for the vaporization of cumene which undergoes dehydrogenation reaction in the reactor (100) or for using as a heat source of a preparation process.

Meanwhile, details concerning the energy saving apparatus for preparing styrene and alpha-methylstyrene concurrently according to the present invention follow the explanation on the energy saving method for preparing styrene and alpha-methylstyrene concurrently.

Mode for Carrying Out the Invention

Hereinafter, preferred embodiments will be suggested to assist the understanding of the present invention, but the following embodiments are only for illustration of the inventive concept, and various changes and modifications can be made by one ordinary skilled in the art within the technical spirit and scope of the present invention, and such changes and modifications are absolutely included in the claims attached herein.

EXAMPLES

Example 1

As shown in FIG. 3A, in a process for preparing styrene and alpha-methylstyrene concurrently by supplying ethylbenzene and cumene concurrently, heat generated in a condenser of an SM/CM separation column was supplied to reactor feed vaporizers, respectively to vaporize ethylbenzene and cumene, heat generated in a condenser of a CM/AMS separation column was supplied to a reboiler of an EB/SM separation column, and a scant amount of heat was supplied using steam. Table 1 below illustrates an injection amount of energy to feed vaporizers and main separation column reboilers in Example 1, and an amount demanded is energy to be supplied to each apparatus and is the same as the sum of reused energy and an injection amount of steam. When the production amounts of styrene and alpha-methylstyrene was 2:1, energy reused in an ethylbenzene vaporizer and a cumene vaporizer was 0.4 Gcal/(SM+AMS) ton, energy reused in an EB/SM separation column was 0.12 Gcal/(SM+AMS) ton, and the total amount of steam supplied to the vaporizers and main separators was 0.78 Gcal/(SM+AMS) ton.

TABLE 1

|  | Energy demanded amount (Gcal/(SM + AMS)ton) | Reused energy amount (Gcal/(SM + AMS)ton) | Steam injection amount (Gcal/(SM + AMS)ton) |
| --- | --- | --- | --- |
| EB vaporizer | 0.22 | 0.2 | 0.02 |
| CM vaporizer | 0.22 | 0.2 | 0.02 |
| SM/CM separation column | 0.44 | — | 0.44 |

TABLE 1-continued

|  | Energy demanded amount (Gcal/(SM + AMS)ton) | Reused energy amount (Gcal/(SM + AMS)ton) | Steam injection amount (Gcal/(SM + AMS)ton) |
| --- | --- | --- | --- |
| EB/SM separation column | 0.30 | 0.12 | 0.18 |
| CM/AMS separation column | 0.12 | — | 0.12 |
| Total | 1.30 | 0.52 | 0.78 |

Example 2

As shown in FIG. 3B, in a process for preparing styrene and alpha-methylstyrene concurrently by supplying ethylbenzene and cumene concurrently, heat generated in a condenser of an EB/SM separation column and a CM/AMS separation column was supplied to reactor feed vaporizers, respectively to vaporize ethylbenzene and cumene, and a scant amount of heat was supplied using steam. Table 2 below illustrates an injection amount of energy to feed vaporizers and main separation column reboilers in Example 2, and an amount demanded is energy to be supplied to each apparatus and is the same as the sum of reused energy and an injection amount of steam. When the production amounts of styrene and alpha-methylstyrene was 2:1, energy reused in an ethylbenzene vaporizer was 0.22 Gcal/(SM+AMS) ton, energy reused in a cumene vaporizer was 0.12 Gcal/(SM+AMS) ton, and the total amount of steam supplied to the vaporizers and main separators was 0.96 Gcal/(SM+AMS) ton. Meanwhile, each component for process streams (or process streams of FIG. 3A and FIG. 3B) of Examples 1 and 2 are shown in Table 3 below. That is, components included in each stream represented by numerals in FIG. 3A and FIG. 3B are shown, and the unit is kg/hr.

TABLE 2

|  | Energy demanded amount (Gcal/(SM + AMS)ton) | Reused energy amount (Gcal/(SM + AMS)ton) | Steam injection amount (Gcal/(SM + AMS)ton) |
| --- | --- | --- | --- |
| EB vaporizer | 0.22 | 0.22 | — |
| CM vaporizer | 0.22 | 0.12 | 0.10 |
| SM/CM separation column | 0.44 | — | 0.44 |
| EB/SM separation column | 0.30 | — | 0.30 |
| CM/AMS separation column | 0.12 | — | 0.12 |
| Total | 1.30 | 0.34 | 0.96 |

TABLE 3

|     | Stream 1 | Stream 2 | Stream 3 | Stream 4 | Stream 5 | Stream 6 | Stream 7 |
|-----|----------|----------|----------|----------|----------|----------|----------|
| EB  | 5,991    | 5,990    | 1        | 5,982    | 8        | 1        | —        |
| SM  | 16,452   | 16,390   | 63       | 125      | 16,265   | 63       | —        |
| CM  | 3,140    | 5        | 3,135    | —        | 5        | 3,126    | 9        |
| AMS | 8,809    | —        | 8,809    | —        | —        | 65       | 8,744    |

Comparative Example 1

If energy was not reused in a process for preparing styrene and alpha-methylstyrene concurrently by supplying ethylbenzene and cumene concurrently, total steam amount injected to an ethylbenzene vaporizer, a cumene vaporizer, an SM/CM separation column, an EB/SM separation column, and a CM/AMS separation column was 1.3 Gcal/(SM+AMS) ton.

Examples 1-2 and Comparative Example 1

As found through Examples 1 and 2 and the comparative example, it is secured that the amount of steam injection, that is, net energy amount required in a process may be saved by appropriately reusing energy during preparing styrene and alpha-methylstyrene concurrently according to the present invention.

The invention claimed is:
1. A method for preparing styrene and alpha-methylstyrene concurrently, the method comprising:
   (a) a step of performing dehydrogenation reaction of ethylbenzene and cumene in the presence of a catalyst;
   (b) a step of recovering heat from a reaction product by the reaction;
   (c) a step of separating a gas phase from at least a portion of a reaction product undergone step (b) and sending thereof to a compression part, separating condensing water including water from a liquid phase, and recovering a fraction including styrene and alpha-methylstyrene;
   (d) a step of compressing and cooling at least a portion of a gas phase among reaction products undergone step (c) to separate components having a low boiling point including hydrogen and carbon dioxide as a gas phase, and recycle a liquid phase including styrene, alpha-methylstyrene, ethylbenzene and cumene to step (c);
   (e) a step of distilling and separating at least a portion of the fraction including styrene and alpha-methylstyrene, which is recover in step (c), into a fraction including styrene and a fraction including unreacted cumene;
   (f) a step of recovering styrene from at least a portion of the fraction including styrene of step (e) and distilling and separating the fraction including unreacted ethylbenzene;
   (g) a step of recovering ethylbenzene from at least a portion of the fraction including unreacted ethylbenzene of step (f) and recycling to a reaction part, and distilling and separating the fraction including benzene and toluene;
   (h) a step of recovering cumene from at least a portion of the fraction including unreacted cumene of step (e) and recycling the recovered cumene to a reaction part, and distilling and separating a fraction including alpha-methylstyrene; and
   (i) a step of recovering alpha-methylstyrene from at least a portion of the fraction including alpha-methylstyrene of step (h), and distilling and separating a fraction including a remaining component having a high boiling point,
   wherein at least one of energy used during the distilling and separating in step (e) and energy used during the distilling and separating in step (h) is recovered to use for the vaporization of ethylbenzene and cumene of step (a) or as a heat source of a preparation process.

2. The method for preparing styrene and alpha-methylstyrene concurrently of claim 1, wherein energy used during the distilling and separating in step (e) and energy used during the distilling and separating in step (h) are heat used for condensation.

3. The method for preparing styrene and alpha-methylstyrene concurrently of claim 1, wherein the distilling in step (e) is performed at 120° C. or less.

4. The method for preparing styrene and alpha-methylstyrene concurrently of claim 1, wherein energy used for the distilling and separating in step (e) is used for the vaporization of ethylbenzene and cumene, which is performed at 100° C. or less.

5. The method for preparing styrene and alpha-methylstyrene concurrently of claim 1, wherein energy used for the distilling and separating in step (h) is used for the distillation in step (f), which is performed at 120° C. or less.

6. The method for preparing styrene and alpha-methylstyrene concurrently of claim 1, wherein the vaporization of ethylbenzene and cumene is performed by further supplying steam.

7. The method for preparing styrene and alpha-methylstyrene concurrently of claim 1, wherein the ratio of ethylbenzene and cumene used for the dehydrogenation reaction is 0.1-10:1 by weight.

8. The method for preparing styrene and alpha-methylstyrene concurrently of claim 1, wherein the dehydrogenation reaction is performed at a temperature of 300 to 800° C.

9. The method for preparing styrene and alpha-methylstyrene concurrently of claim 1, wherein the reaction product of step (b) is cooled to 15 to 60° C.

10. The method for preparing styrene and alpha-methylstyrene concurrently of claim 1, wherein the reaction product of step (d) is compressed until a pressure reaches 1.5 to 5.5 KCA.

11. An apparatus for preparing styrene and alpha-methylstyrene concurrently, the apparatus comprising:
   a reactor for performing dehydrogenation reaction of ethylbenzene and cumene in the presence of catalyst;
   a heat exchanger for recovering heat from a reaction product from the reaction;
   a decanter for separating a gas phase from at least a portion of a reaction product from which heat is recovered and sending thereof to a compression part, for separating condensing water including water from a liquid phase, and for recovering a fraction including styrene and alpha-methylstyrene;
   a compression part composed of a compressor, a heat exchanger and a drum, for compressing and cooling at least a portion of the separated gas phase to separate components having a low boiling point including hydrogen and carbon dioxide as a gas phase, and for recovering a liquid phase including styrene, alpha-methylstyrene, ethylbenzene and cumene;

an SM/CM separation column for distilling and separating at least a portion of the fraction including styrene and alpha-methylstyrene, supplied from the decanter into a fraction including styrene and a fraction including unreacted cumene;

an EB/SM separation column for recovering styrene from at least a portion of the fraction including styrene separated from the SM/CM separation column, and distilling and separating a fraction including unreacted ethylbenzene;

an EB purification column for recovering ethylbenzene from at least a portion of the fraction including unreacted ethylbenzene, separated from the EB/SM separation column and recycling the recovered ethylbenzene to the reactor, and distilling and separating a fraction including benzene and toluene;

a CM/AMS separation column for recovering cumene from at least a portion of the fraction including unreacted cumene, separated from the SM/CM separation column, and recycling the recovered cumene to the reactor, and distilling and separating a fraction including alpha-methylstyrene;

an AMS purification column for recovering alpha-methylstyrene from at least a portion of the fraction including alpha-methylstyrene, separated from the CM/AMS separation column, and distilling and separating a fraction including a remaining component having a high boiling point;

an EB vaporizer for receiving energy used in the SM/CM separation column and the CM/AMS separation column, and for using the energy for the vaporization of ethylbenzene which undergoes dehydrogenation reaction in the reactor or for using as a heat source of a preparation process; and a CM vaporizer for receiving energy used in the SM/CM separation column and the CM/AMS separation column, and for using for the vaporization of cumene which undergoes dehydrogenation reaction in the reactor or for using as a heat source of a preparation process.

12. The apparatus for preparing styrene and alpha-methylstyrene concurrently of claim 11, wherein the energy used in the SM/CM separation column and the CM/AMS separation column is heat used in each condenser of the SM/CM separation column and the CM/AMS separation column.

13. The apparatus for preparing styrene and alpha-methylstyrene concurrently of claim 11, wherein the distilling of the SM/CM separation column is performed at 120° C. or less.

14. The apparatus for preparing styrene and alpha-methylstyrene concurrently of claim 11, wherein the energy used in the SM/CM separation column is supplied to the EB vaporizer and the CM vaporizer, which are operated at 100° C. or less.

15. The apparatus for preparing styrene and alpha-methylstyrene concurrently of claim 11, wherein the energy used in the CM/AMS separation column is supplied to the EB/SM separation column, which is operated at 120° C. or less.

16. The apparatus for preparing styrene and alpha-methylstyrene concurrently of claim 11, wherein a pressure of the SM/CM separation column is from 0.01 to 5 KCA.

17. The apparatus for preparing styrene and alpha-methylstyrene concurrently of claim 11, wherein a pressure of the EB/SM separation column is from 0.01 to 6 KCA.

18. The apparatus for preparing styrene and alpha-methylstyrene concurrently of claim 11, wherein a pressure of the AMS purification column is from 0.01 to 9 KCA.

19. The apparatus for preparing styrene and alpha-methylstyrene concurrently of claim 11, wherein a pressure of the CM/AMS separation column is from 0.01 to 8 KCA.

20. The apparatus for preparing styrene and alpha-methylstyrene concurrently of claim 11, wherein a pressure of the EB purification column is from 0.01 to 7 KCA.

* * * * *